United States Patent
Kang et al.

(10) Patent No.: US 11,301,043 B2
(45) Date of Patent: Apr. 12, 2022

(54) IMPLANTABLE DEVICE AND OPERATING METHOD OF IMPLANTABLE DEVICE

(71) Applicant: Samsung Electronics Co., Ltd., Suwon-si (KR)

(72) Inventors: Joonseong Kang, Suwon-si (KR); Sang Joon Kim, Hwaseong-si (KR)

(73) Assignee: Samsung Electronics Co., Ltd, Suwon-si (KR)

(*) Notice: Subject to any disclaimer, the term of this patent is extended or adjusted under 35 U.S.C. 154(b) by 371 days.

(21) Appl. No.: 16/590,405

(22) Filed: Oct. 2, 2019

(65) Prior Publication Data

US 2020/0363870 A1 Nov. 19, 2020

(30) Foreign Application Priority Data

May 17, 2019 (KR) .................. 10-2019-0057804

(51) Int. Cl.
*G06F 3/01* (2006.01)
*G06N 3/06* (2006.01)
*G06Q 20/06* (2012.01)
*A61B 5/389* (2021.01)
*G06Q 20/38* (2012.01)
*G06Q 20/32* (2012.01)

(52) U.S. Cl.
CPC .............. *G06F 3/015* (2013.01); *A61B 5/389* (2021.01); *G06N 3/061* (2013.01); *G06Q 20/06* (2013.01); *G06Q 20/321* (2020.05); *G06Q 20/3825* (2013.01); *G06Q 2220/00* (2013.01)

(58) Field of Classification Search
CPC ..... G06F 3/015; A61B 5/389; A61B 5/14503; A61B 5/37; A61B 5/293; A61B 5/24; A61B 5/316; A61B 5/369; A61B 5/7235; G06N 3/061; G06Q 20/06; G06Q 20/321; G06Q 20/3825; G06Q 2220/00; G06Q 20/065; G06Q 20/363; G06Q 20/382
USPC ........................................................ 705/69
See application file for complete search history.

(56) References Cited

U.S. PATENT DOCUMENTS

| 9,672,499 | B2 | 6/2017 | Yang et al. | |
|---|---|---|---|---|
| 2004/0054297 | A1* | 3/2004 | Wingeier | A61B 5/374 600/544 |
| 2009/0118597 | A1* | 5/2009 | Mills | A61B 5/0031 600/301 |
| 2011/0136076 | A1 | 6/2011 | Li | |
| 2018/0121892 | A1 | 5/2018 | Dwivedi et al. | |

(Continued)

FOREIGN PATENT DOCUMENTS

| KR | 10-1699130 B1 | 1/2017 |
|---|---|---|
| KR | 10-2018-0072350 A | 6/2018 |

OTHER PUBLICATIONS

Kim, "Sweden: Thousands of microchips implanted in skin", May 14, 2018 http://www.etnews.com/20180514000248, , Last visited Oct. 1, 2019 (2 pages in English and 2 pages in Korean).

(Continued)

*Primary Examiner* — Zeshan Qayyum
(74) *Attorney, Agent, or Firm* — NSIP Law

(57) ABSTRACT

An method of operating an implantable device includes sensing a neural signal generated in a tissue of a body, recognizing input information to process a cryptocurrency-based financial transaction by analyzing the sensed neural signal, and processing the cryptocurrency-based financial transaction based on the recognized input information.

22 Claims, 11 Drawing Sheets

(56) References Cited

U.S. PATENT DOCUMENTS

2018/0253151 A1    9/2018  Kletsov et al.
2018/0293837 A1*  10/2018  Hoehne ............... G07F 17/3223
2019/0286592 A1*   9/2019  Seo ......................... A61B 5/24

OTHER PUBLICATIONS

Pettit, Harry et al., "Would you have a microchip implanted under your Skin? 3,000 Swedes with electronic tags embedded into their hands risk their personal data being used against them", May 14, 2018, https://www.dailymail.co.uk/sciencetech/article-5726197/Would-microchip-SKIN-3-000-Swedes-electronic-tag-embedded-hands.html, last visited on Oct. 1, 2019 (6 pages in English).
"KeepKey", https://shapeshift.io/keepkey/, last visited Oct. 1, 2019 (3 pages in English).
"Ledger Nano S", https://www.ledger.com/, last visited Oct. 1, 2019 (3 pages in English).

* cited by examiner

IMPLANTABLE DEVICE AND OPERATING METHOD OF IMPLANTABLE DEVICE

CROSS-REFERENCE TO RELATED APPLICATIONS

This application claims the benefit under 35 USC § 119(a) of Korean Patent Application No. 10-2019-0057804 filed on May 17, 2019, in the Korean Intellectual Property Office, the entire disclosure of which is incorporated herein by reference for all purposes.

BACKGROUND

Field

The following description relates to an implantable device and an operating method of the implantable device.

Description of Related Art

The use of cryptocurrency is increasing in society, and a value of the cryptocurrency is also growing. However, cryptocurrencies are vulnerable to security risks due to their centralized form. To address these security vulnerability, there have been various attempts, such as, for example, introducing a distributed system and applying methods of security technology such as embodying electronic money in a form of interconnected message, such as a blockchain.

Despite such attempts, hacking incidents are still continuing for cryptocurrencies, and for an electronic wallet, that may store these cryptocurrencies. To safely protect the electronic wallet, a widely used method is a cold wallet which refers to storing the electronic wallet in a separate device such as a universal serial bus (USB) that is not connected to the Internet. However, such cold wallet method may be inconvenient because the separate device needs to be carried around all the time to use a cryptocurrency, and there is a risk of it being lost or stolen.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a method of operating an implantable device, including sensing a neural signal generated in a tissue of a body, recognizing input information to process a cryptocurrency-based financial transaction by analyzing the sensed neural signal, and processing the cryptocurrency-based financial transaction based on the recognized input information.

The neural signal may be generated based on at least one of an intention of a user or a muscular movement based on the intention of the user.

The neural signal may include at least one of an electrical signal in the body including an electroencephalogram (EEG) signal and an electromyogram (EMG) signal, or a chemical signal in the body including a hormone and a neurotransmitter.

The sensing of the neural signal may include sensing the neural signal or a change in the neural signal using a sensor of the implantable device implanted in the tissue of the body.

The sensing of the neural signal may include at least one of sensing a neural signal generated to induce a movement of the tissue based on an intention of a user, sensing a neural signal generated in a portion of the body of the user based on any one or any combination of the intention of the user or a muscular movement based on the intention of the user, sensing a neural signal generated in a pattern based on any one or any combination of the intention of the user or the muscular movement based on the intention of the user, or sensing a neural signal generated in a pattern in at least one portion of the body of the user based on at least one of the intention of the user or the muscular movement based on the intention of the user.

The sensing of the neural signal may include sensing neural signals through channels in the tissue of the body of the user.

The recognizing of the input information may include analyzing whether the neural signal is a first neural signal corresponding to making a payment with a cryptocurrency, a second neural signal corresponding to transferring the cryptocurrency, or a third neural signal corresponding to a financial transaction not involving the cryptocurrency.

The recognizing of the input information may include recognizing the input information as being for controlling the implantable device to make a payment with the cryptocurrency, in response to the neural signal being the first neural signal.

The recognizing of the input information may include recognizing the input information as being for drafting an invoice for a first account address to which the cryptocurrency is to be transferred, in response to the neural signal being the second neural signal.

The processing of the cryptocurrency-based financial transaction may include receiving the account address to which the cryptocurrency is to be transferred, generating the invoice corresponding to the first account address based on cryptocurrency-related information including a second account address of the cryptocurrency of the user and a private key of the user, and performing an electronic signature on the invoice by generating electronic signature information.

The recognizing of the input information may include recognizing the input information as being for processing the financial transaction, in response to the neural signal being the third neural signal.

The processing of the cryptocurrency-based financial transaction may include inputting a password to process the financial transaction, and performing an electronic signature to process the financial transaction by generating electronic signature information.

The method may include generating a stimulus signal to transfer a result of processing the cryptocurrency-based financial transaction to the body of a user, and recognizing the result of processing the cryptocurrency-based financial transaction, in response to the generated stimulus signal.

The generating of the stimulus signal may include at least one of generating a neural stimulus signal associated with an involuntary muscle of the user, generating a neural stimulus signal connected to a portion of the body of the user, generating a neural stimulus signal to induce a movement of a muscle not intended by the user, generating a stimulus signal to induce a movement in a pattern for a muscle not intended by the user, or generating a neural stimulus signal to induce a tactile stimulus not experienced by the user.

The recognizing of the result of the processing of the cryptocurrency-based financial transaction further may include determining whether an amount of information of the result of processing the cryptocurrency-based financial transaction exceeds a processing capacity of the implantable device, and recognizing the result of processing the cryptocurrency-based financial transaction using an external device, in response to a determination that the amount of the information exceeds the processing capacity of the implantable device.

In another general aspect, there is provided an implantable device including at least one sensor configured to sense a neural signal generated in a tissue of a body, and a processor configured to recognize input information to process a cryptocurrency-based financial transaction by analyzing the neural signal, and to process the cryptocurrency-based financial transaction based on the recognized input information.

The at least one sensor may be configured to sense a neural signal generated to induce a movement of the tissue based on an intention of a user, sense a neural signal generated in a portion of the body of the user based on any one or any combination of the intention of the user or a muscular movement based on the intention of the user, sense a neural signal generated in a pattern based on any one or any combination of the intention of the user or the muscular movement based on the intention of the user, or sense a neural signal generated in a pattern in at least one portion of the body of the user based on at least one of the intention of the user or the muscular movement based on the intention of the user.

The processor may be configured to analyze whether the neural signal is a first neural signal corresponding to making a payment with a cryptocurrency, a second neural signal corresponding to transferring the cryptocurrency, or a third neural signal corresponding to a financial transaction not involving the cryptocurrency.

The processor may be configured to recognize the input information as being for controlling the implantable device to make a payment with the cryptocurrency, in response to the neural signal being the first neural signal, recognize the input information as being for drafting an invoice for a first account address to which the cryptocurrency is to be transferred, in response to the neural signal being the second neural signal, and recognize the input information as being for processing the financial transaction, in response to the neural signal being the third neural signal.

The implantable device may include a stimulus generator configured to generate a stimulus signal to transfer a result of processing the cryptocurrency-based financial transaction to the body of a user, and the processor is further configured to recognize the result of processing the cryptocurrency-based financial transaction, in response to the generated stimulus signal.

The stimulus signal may include at least one of a neural stimulus signal associated with an involuntary muscle of the user, a neural stimulus signal connected to a portion of the body of the user, a neural stimulus signal to induce a movement of a muscle not intended by the user, a stimulus signal to induce a movement in a pattern for a muscle not intended by the user, or a neural stimulus signal to induce a tactile stimulus not experienced by the user.

The processor may be configured to determine whether an amount of information of the result of processing the cryptocurrency-based financial transaction exceeds a processing capacity of the implantable device, and recognize the result of processing the cryptocurrency-based financial transaction by further using an external device, in response to a determination that the amount of the information exceeds the processing capacity of the implantable device.

The implantable device may include a memory configured to store cryptocurrency-related information comprising at least one of a private key of the user or an account address of a cryptocurrency of the user.

Other features and aspects will be apparent from the following detailed description, the drawings, and the claims.

Figure 1A:
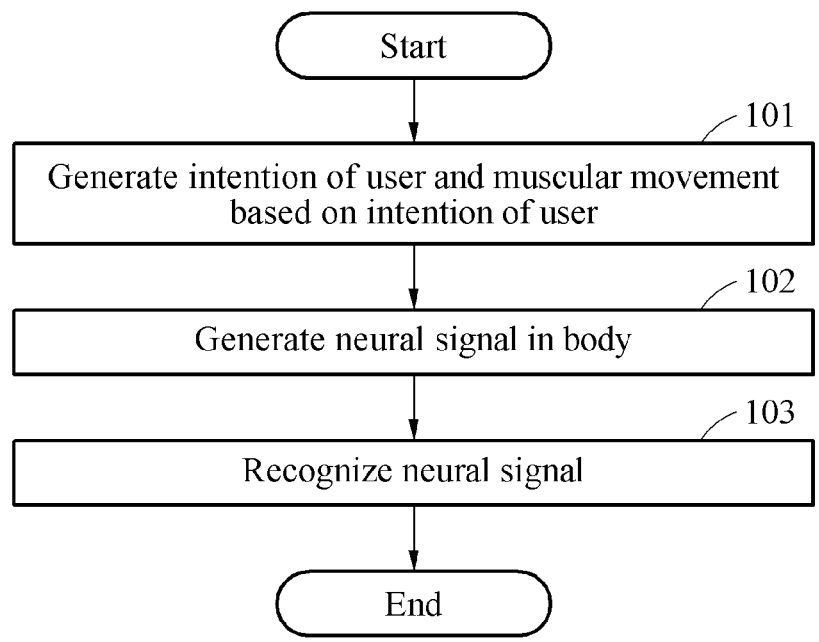
FIGS. 1A and 1B are diagrams illustrating examples of an operating method of an implantable device.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known after an understanding of the disclosure of this application may be omitted for increased clarity and conciseness.

The features described herein may be embodied in different forms and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Throughout the specification, when a component is described as being "connected to," or "coupled to" another component, it may be directly "connected to," or "coupled to" the other component, or there may be one or more other components intervening therebetween. In contrast, when an element is described as being "directly connected to," or "directly coupled to" another element, there can be no other elements intervening therebetween. Likewise, similar expressions, for example, "between" and "immediately between," and "adjacent to" and "immediately adjacent to," are also to be construed in the same way. As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

The terminology used herein is for describing various examples only and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

The use of the term "may" herein with respect to an example or embodiment (e.g., as to what an example or embodiment may include or implement) means that at least one example or embodiment exists where such a feature is included or implemented, while all examples are not limited thereto.

Also, in the description of example embodiments, detailed description of structures or functions that are thereby known after an understanding of the disclosure of the present application will be omitted when it is deemed that such description will cause ambiguous interpretation of the example embodiments.

Hereinafter, examples will be described in detail with reference to the accompanying drawings, and like reference numerals in the drawings refer to like elements throughout.

Figure 1B:
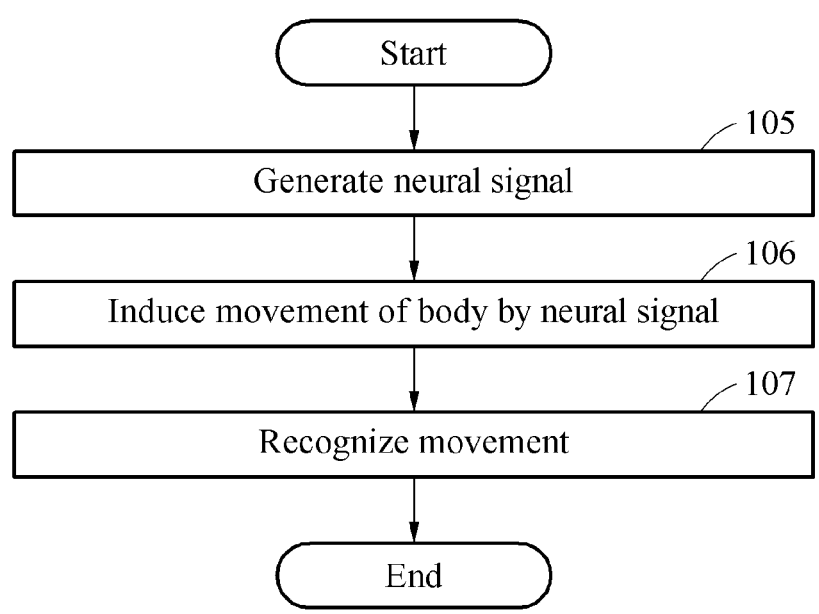

FIGS. 1A and 1B are diagrams illustrating examples of an operating method of an implantable device. FIG. 1A illustrates how an implantable device that is implanted in a body of a user receives information input or transmitted from the user.

The user may induce or cause a change in biosignal by controlling the body of the user to transfer information to the implantable device that is implanted in the body of the user. The implantable device may recognize such change in biosignal and receive the information. The implantable device may be, for example, an electronic wallet configured to store and/or manage a private key input by the user to approve the use of a cryptocurrency. In an example, the implantable device may be the same as the electronic wallet. The implantable device may also be simply referred to as a device.

In an example, the electronic wallet for the approval of the use of a cryptocurrency is implemented by an implantable device and the user's biosignal is used as an interface. Thus, it is possible to prevent the electronic wallet from being hacked, and reduce the inconvenience of carrying an additional device as the electronic wallet by provided an implantable device as a type of cold wallet. This also minimizes the risk of the additional device being lost or stolen.

The operations in FIG. 1A may be performed in the sequence and manner as shown, although the order of some operations may be changed or some of the operations omitted without departing from the spirit and scope of the illustrative examples described. Many of the operations shown in FIG. 1A may be performed in parallel or concurrently. One or more blocks of FIG. 1A, and combinations of the blocks, can be implemented by special purpose hardware-based computer, such as a processor, that perform the specified functions, or combinations of special purpose hardware and computer instructions. In addition to the description of FIG. 1A below, the descriptions of FIGS. 1-10 are also applicable to FIG. 11 and are incorporated herein by reference. Thus, the above description may not be repeated here.

Referring to FIG. 1A, in operation 101, the user generates an intention of the user and a muscular movement based on the intention of the user to control the implantable device implanted in the body of the user and inputs information needed for the use of a cryptocurrency, for example, an account to which the cryptocurrency is to be transferred. In operation 102, the intention of the user and/or the muscular movement generates a neural signal in the body of the user. The neural signal may be generated based on at least one of the intention of the user or the muscular movement based on the intention of the user. The neural signal may include an electrical signal in the body including, for example, an electroencephalogram (EEG) signal and an electromyogram (EMG) signal, and also a chemical signal in the body including a hormone and a neurotransmitter.

In operation 103, when the neural signal that is adjustable by the intention of the user is generated, the implantable device recognizes the neural signal, and receives the information transmitted from the user to the implantable device. For example, the implantable device may recognize, as the input information, an EMG signal that is generated when the user moves his/her hand or foot, or a neural signal intending a movement of his/her hand or foot.

FIG. 1B illustrates how an implantable device implanted in a body of a user outputs information to the user. The operations in FIG. 1B may be performed in the sequence and manner as shown, although the order of some operations may be changed or some of the operations omitted without departing from the spirit and scope of the illustrative examples described. Many of the operations shown in FIG. 1B may be performed in parallel or concurrently. One or more blocks of FIG. 1B, and combinations of the blocks, can be implemented by special purpose hardware-based computer, such as a processor, that perform the specified functions, or combinations of special purpose hardware and computer instructions.

The implantable device may stimulate a tissue of a body of a user through a stimulator to transfer information to the user, and the user may receive the information by recognizing the stimulation.

Referring to FIG. 1B, when the implantable device implanted in the body of the user is to transfer information to the user, the implantable device generates a neural signal in operation 105. In operation 106, the implantable device induces a movement of the body of the user by the neural signal in The implantable device may induce the movement of the body of the user by, for example, changing a biosignal that is not controllable by an intention of the user, e.g., an involuntary muscle, through a stimulator, for example, a stimulator 540 illustrated in FIG. 5. In another example, implantable device may change a biosignal that is not intended by the user through a stimulus provided by the stimulator. The user recognizes the movement induced by the implantable device in operation 107, and receives the information transferred from the implantable device. In this example, the biosignal that is not controllable by an intention of a user may be, for example, a biosignal associated with an involuntary muscle of the user and a tactile stimulus signal without contact with the user.

In an example, an external device, in lieu of or in addition to the user, may recognize the movement induced by the implantable device. For example, when the implantable device stimulates a muscle under the eye, which is an involuntary muscle, the user and/or an external camera may recognize a movement by a stimulus provided to the muscle under eye of the user and receive information of the stimulus.

In an example, by applying a neural signal of a user as an interface that requires a high level of security between the user and an implantable device operating as an electronic wallet, it is possible to reduce inconvenience in carrying an additional device to use a cryptocurrency and reduce a risk of the device being lost or stolen while achieving a high level of security. The implantable device may be applied to a cryptocurrency system that uses the implantable device as the electronic wallet.

Figure 2:
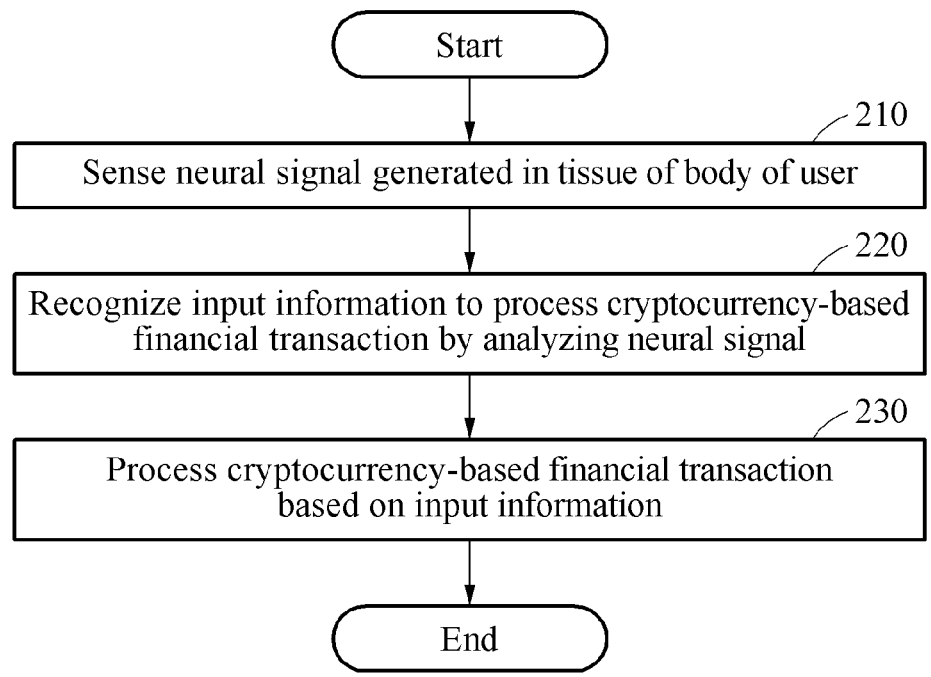
FIG. 2 is a diagram illustrating an example of an operating method of an implantable device.

FIG. 2 is a diagram illustrating an example of an operating method of an implantable device. The operations in FIG. 2 may be performed in the sequence and manner as shown, although the order of some operations may be changed or some of the operations omitted without departing from the spirit and scope of the illustrative examples described. Many of the operations shown in FIG. 2 may be performed in parallel or concurrently. One or more blocks of FIG. 2, and combinations of the blocks, can be implemented by special purpose hardware-based computer, such as a processor, that perform the specified functions, or combinations of special purpose hardware and computer instructions. In addition to the description of FIG. 2 below, the descriptions of FIGS. 1A-1B are also applicable to FIG. 2 and are incorporated herein by reference. Thus, the above description may not be repeated here.

Referring to FIG. 2, in operation 210, an implantable device senses at least one neural signal generated in a tissue of a body of a user. For example, the implantable device may sense at least one of a neural signal or a change in neural signal, using at least one sensor of the implantable device implanted in the issue of the body of the user.

In operation 210, the implantable device may sense, for example, a neural signal that is generated to induce a movement of the tissue of the body based on an intention the user. The implantable device may sense a neural signal that is generated in at least a portion of the body of the user based on at least one of the intention of the user or a muscular movement based on the intention of the user. In an example, the implantable device may sense a neural signal that is generated in a certain pattern based on at least one of the intention of the user or the muscular movement based on the intention of the user. In addition, the implantable device may sense a neural signal that is generated in a certain pattern in at least a portion of the body of the user based on at least one of the intention of the user or the muscular movement based on the intention of the user. In an example, the implantable device may sense a plurality of neural signals in the tissue of the body of the user through a plurality of channels.

In an example, the implantable device may determine whether an amount of detected neural signals exceed a processing capacity of the implantable device. In an example, the amount of detected neural signals may refer to any one or any combination of an amount encompassing the number of occurrence of neural signals, the number of regions portions in which neural signals occur, and a signal amount of neural signals. For example, a case in which the amount of sensed neural signals exceeds the processing capacity of the implantable device may include a case in which a neural signal is sensed through the number of channels that exceeds a preset number of channels, or a case in which an amount of change in neural signal exceeds a threshold. When it is determined that the amount of sensed neural signals exceeds the processing capacity of the implantable device, the implantable device may sense the neural signal by further using an external device.

In operation 220, the implantable device recognizes input information to process a cryptocurrency-based financial transaction by analyzing the neural signal sensed in operation 210. The implantable device may analyze the neural signal to recognize which financial transaction is to be processed based on the neural signal as the input information. For example, the implantable device may analyze whether the neural signal is a first neural signal corresponding to a function of making a payment with a cryptocurrency, a second neural signal corresponding to a function of transferring the cryptocurrency, or a third neural signal corresponding to another financial transaction that does not involve the cryptocurrency. In an example, a function corresponding to each neural signal may be determined in advance and stored in a memory.

In an example, when the neural signal is the first neural signal, the implantable device may recognize the neural signal as input information to control the implantable device, which is an electronic wallet, to make a payment with a cryptocurrency. In an example, when the neural signal is the second neural signal, the implantable device may recognize the neural signal as input information to draft an invoice corresponding to a first account address to which a cryptocurrency is to be transferred. In an example, when the neural signal is the third neural signal, the implantable device may recognize the neural signal as input information to process a financial transaction that does not involve a cryptocurrency.

The other financial transaction may include transactions, such as, for example, remittance, transfer, and payment for an actually circulated currency. Financial transactions involving both actually circulated currency and cryptocurrency may be performed using blockchain technology, but may be determined based on whether a target to be processed is a cryptocurrency or an actual currency.

For example, the first neural signal, the second neural signal, and the third neural signal may be neural signals corresponding to different body portions, for example, a hand, a face, and a leg. For example, the first neural signal, the second neural signal, and the third neural signal may be neural signals corresponding to different patterns, for example, a pattern of turning a second finger, a pattern of bending all five fingers, and a pattern of unfolding one or more of the five fingers, of a body portion, for example, a hand.

In operation 230, the implantable device processes the cryptocurrency-based financial transaction based on the input information recognized in operation 220. In an example, the cryptocurrency-based financial transaction may be construed as encompassing various financial transactions, such as, for example, deposit, payment, and transfer, based on blockchain technology, in addition to a cryptocurrency transaction processed in a distributed system-based way using the blockchain technology. The cryptocurrency-based financial transaction may also be construed as encompassing all financial transactions including remittance, transfer, and payment of an actually circulated currency in addition to a cryptocurrency.

For example, in operation 220, when the neural signal is recognized as input information to control the implantable device corresponding to the electronic wallet, in operation 230, the implantable device controls the electronic wallet based on information transmitted from the user.

In another example, in operation 220, when the neural signal is recognized as input information to draft an invoice corresponding to a first account address of a counterpart to which a cryptocurrency is to be transferred, in operation 230, the implantable device operates as follows. In operation 230, in response to the second neural signal, the implantable device receives the first account address to which the cryptocurrency is to be transferred. The implantable device generates the invoice corresponding to the first account address based on cryptocurrency-related information including a second account address of a cryptocurrency of the user and a private key of the user. The implantable device performs an electronic signature on the invoice by generating electronic signature information.

In another examples, in operation 220, when the neural signal is recognized as input information to process another financial transaction not involving a cryptocurrency, the implantable device operates as follows in operation 230. In operation 230, the implantable device inputs a password to process or perform the other financial transaction, or perform an electronic signature for the other financial transaction not involving the cryptocurrency by generating the electronic signature information.

Figure 3:
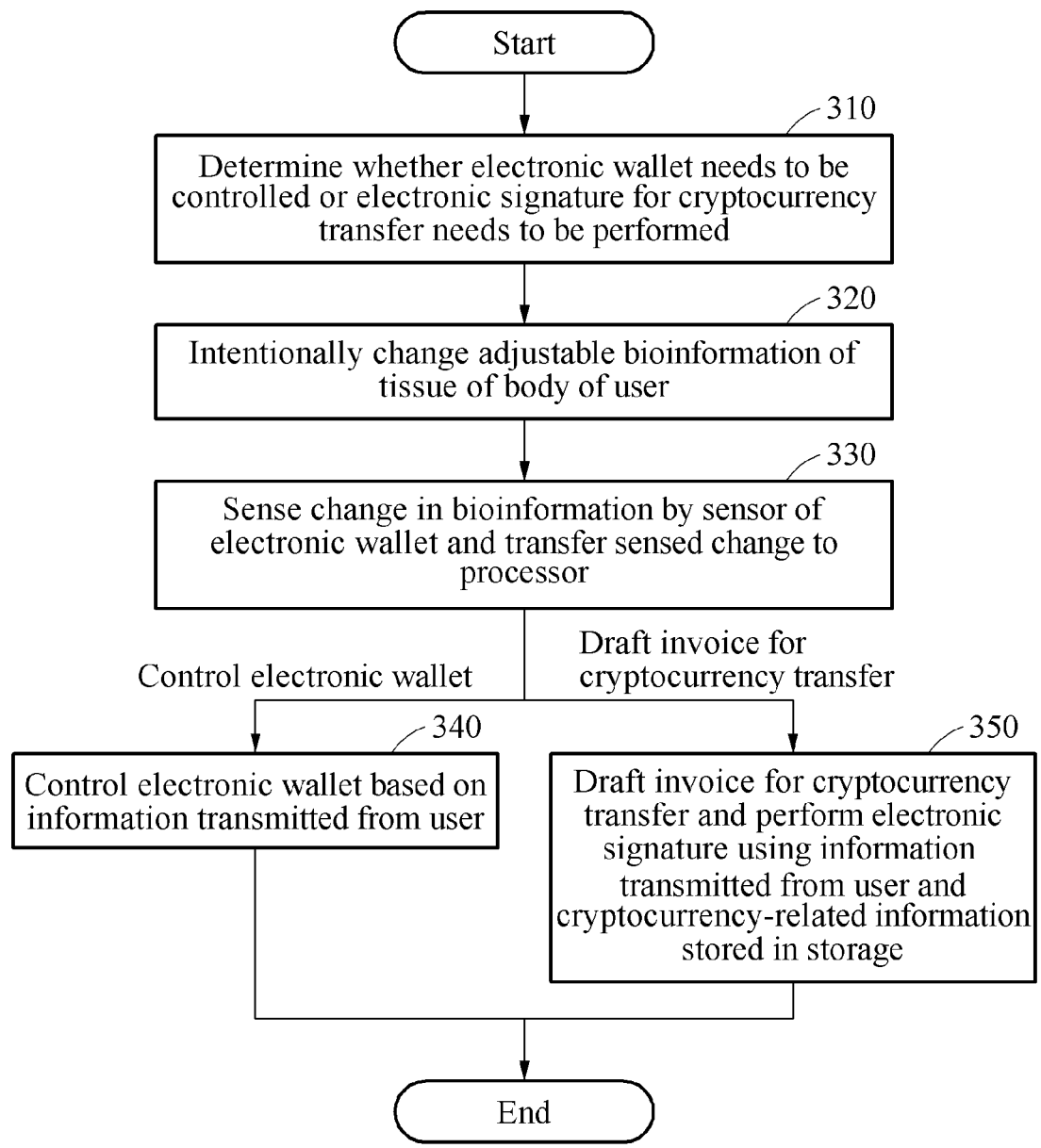
FIGS. 3 and 4 are diagrams illustrating examples of an operating method of an implantable device.

FIG. 3 is a diagram illustrating an example of an operating method of an implantable device. The operations in FIG. 3 may be performed in the sequence and manner as shown, although the order of some operations may be changed or some of the operations omitted without departing from the spirit and scope of the illustrative examples described. Many of the operations shown in FIG. 3 may be performed in parallel or concurrently. One or more blocks of FIG. 3, and combinations of the blocks, can be implemented by special purpose hardware-based computer, such as a processor, that perform the specified functions, or combinations of special purpose hardware and computer instructions. In addition to the description of FIG. 3 below, the descriptions of FIGS. 1A-2 are also applicable to FIG. 3 and are incorporated herein by reference. Thus, the above description may not be repeated here. Hereinafter, an example of how an implantable device operates when a user transmits information to the implantable device corresponding to an electronic wallet will be described with reference to FIG. 3.

In operation 310, when it is determined that the electronic wallet needs to be controlled, or an invoice needs to be drafted to transfer a cryptocurrency and/or an electronic signature needs to be performed, in operation 320, a user intentionally changes adjustable bioinformation of a tissue of a body of the user. For example, the user stimulates the tissue of the user as intended by, for example, tensing muscles of arms or legs of the user for a number of times, or moving a hand, a foot, or fingers of the user in a certain pattern as intended. As described above, the user may have an intention of moving the tissue of the body of the user to generate a neural signal, and change various sets of bioinformation of the tissue by the neural signal.

Figure 5:
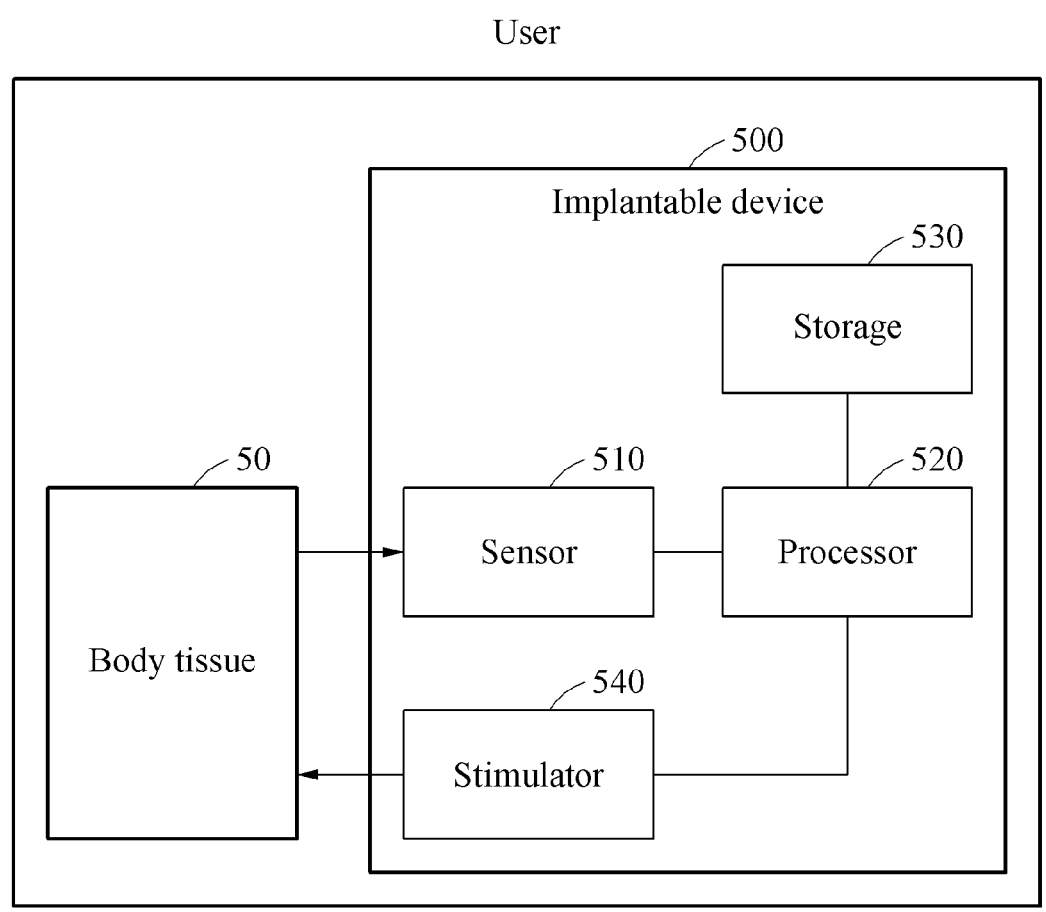
FIG. 5 is a diagram illustrating an example of an implantable device.

In operation 330, a sensor, for example, a sensor 510 illustrated in FIG. 5, in the electronic wallet senses a change in bioinformation of the user and transfers the sensed change to a processor, for example, a processor 520 illustrated in FIG. 5. The change in bioinformation may be construed as encompassing some or all changes in various sensory signals including senses of sight, hearing, touch, smell, and taste, in addition to a change in neural signal such as, for example, an EEG signal, an EMG signal, and a vagal nerve signal. The processor receives the information transmitted from the user based on the change in bioinformation.

For example, when the information received in operation 330 corresponds to a control signal of the electronic wallet, the electronic wallet is controlled based on the information transmitted from the user in operation 340. For another example, when the information received in operation 330 corresponds to an invoice drafting signal to transfer a cryptocurrency, the electronic wallet drafts an invoice to transfer the cryptocurrency and performs an electronic signature using the information transmitted from the user and cryptocurrency-related information stored in a storage in operation 350. In this example, the information transmitted from the user may include, for example, an account address of a cryptocurrency of the user, a private key of the user, and the like.

Figure 4:
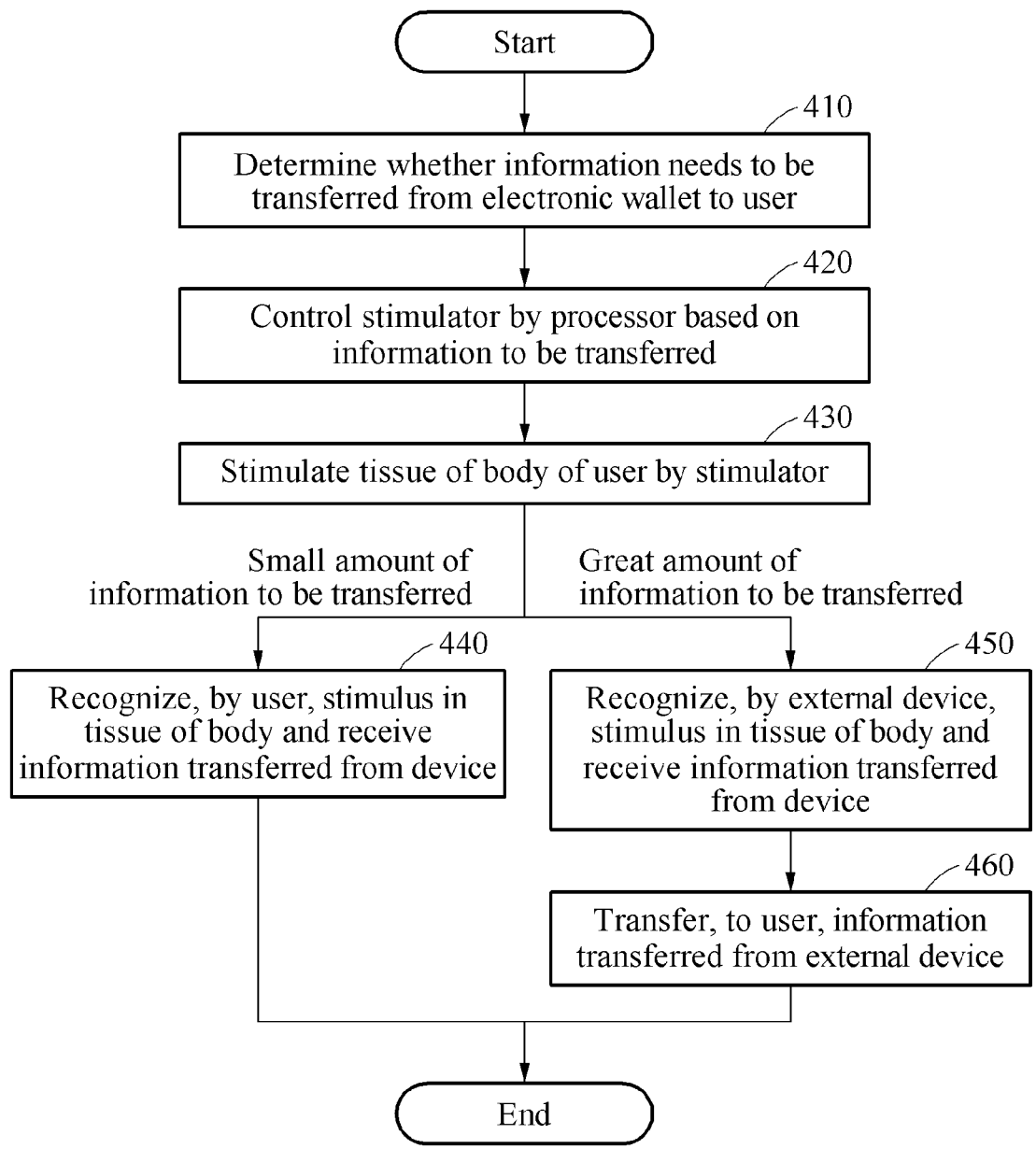

FIG. 4 is a diagram illustrating another example of an operating method of an implantable device. The operations in FIG. 4 may be performed in the sequence and manner as shown, although the order of some operations may be changed or some of the operations omitted without departing from the spirit and scope of the illustrative examples described. Many of the operations shown in FIG. 4 may be performed in parallel or concurrently. One or more blocks of FIG. 4, and combinations of the blocks, can be implemented by special purpose hardware-based computer, such as a processor, that perform the specified functions, or combinations of special purpose hardware and computer instructions. In addition to the description of FIG. 4 below, the descriptions of FIGS. 1A-3 are also applicable to FIG. 4 and are incorporated herein by reference. Thus, the above description may not be repeated here. Hereinafter, FIG. 4 describes an example of how an implantable device corresponding to an electronic wallet transfers information to a user.

Referring to FIG. 4, in operation 410, the electronic wallet needs to transfer information to the user. In an example, the information may need to be transferred to the user, for example, when a result of controlling the electronic wallet needs to be reported to the user, or when an invoice drafted to transfer a cryptocurrency needs to be transferred to the user, as described above with reference to FIG. 3.

When the information needs to be transferred, in operation 420, a processor of the electronic wallet controls a stimulator, for example, a stimulator 540 illustrated in FIG. 5, based on the information that is to be transferred to the user. In operation 430, the stimulator of the electronic wallet stimulates a tissue of a body of the user. The electronic wallet may induce a movement of the tissue of the body of the user by stimulating a muscle of the tissue or stimulate a neural signal connected to the tissue. The electronic wallet may induce a change in the tissue of the body of the user by controlling the stimulator of the electronic wallet. The user may recognize the transfer of the information from the electronic wallet based on a movement of an involuntary muscle that the user is not able to control voluntarily, an unintended muscular movement, or a tactile signal that is not experienced by the user. The information to be transferred to the user may correspond to, for example, a result of processing or performing a cryptocurrency-based financial transaction.

In an example, the electronic wallet may determine whether an amount of the information of the result of performing the cryptocurrency-based financial transaction exceeds a processing capacity of the implantable device. When it is determined that the amount of the information of the result of performing the cryptocurrency-based financial transaction exceeds the processing capacity of the implantable device, the electronic wallet may allow the user to recognize the result of performing the cryptocurrency-based financial transaction using an external device.

When it is determined that the amount of the information to be transferred to the user is relatively small compared to a preset standard, in operation 440, the electronic wallet may allow the user to recognize a stimulus in the tissue of the user and directly receive the information transferred from the electronic wallet. The amount of the information to be transferred to the user may correspond to, for example, the amount of information of the result of processing the cryptocurrency-based financial transaction.

When it is determined that the amount of the information to be transferred to the user is greater than or equal to the preset standard, in operation 450, the electronic wallet may allow the external device to recognize a stimulus in the tissue and receive the information transferred from the electronic wallet. The information transferred from the external device is transferred to the user in operation 460.

Figure 6:
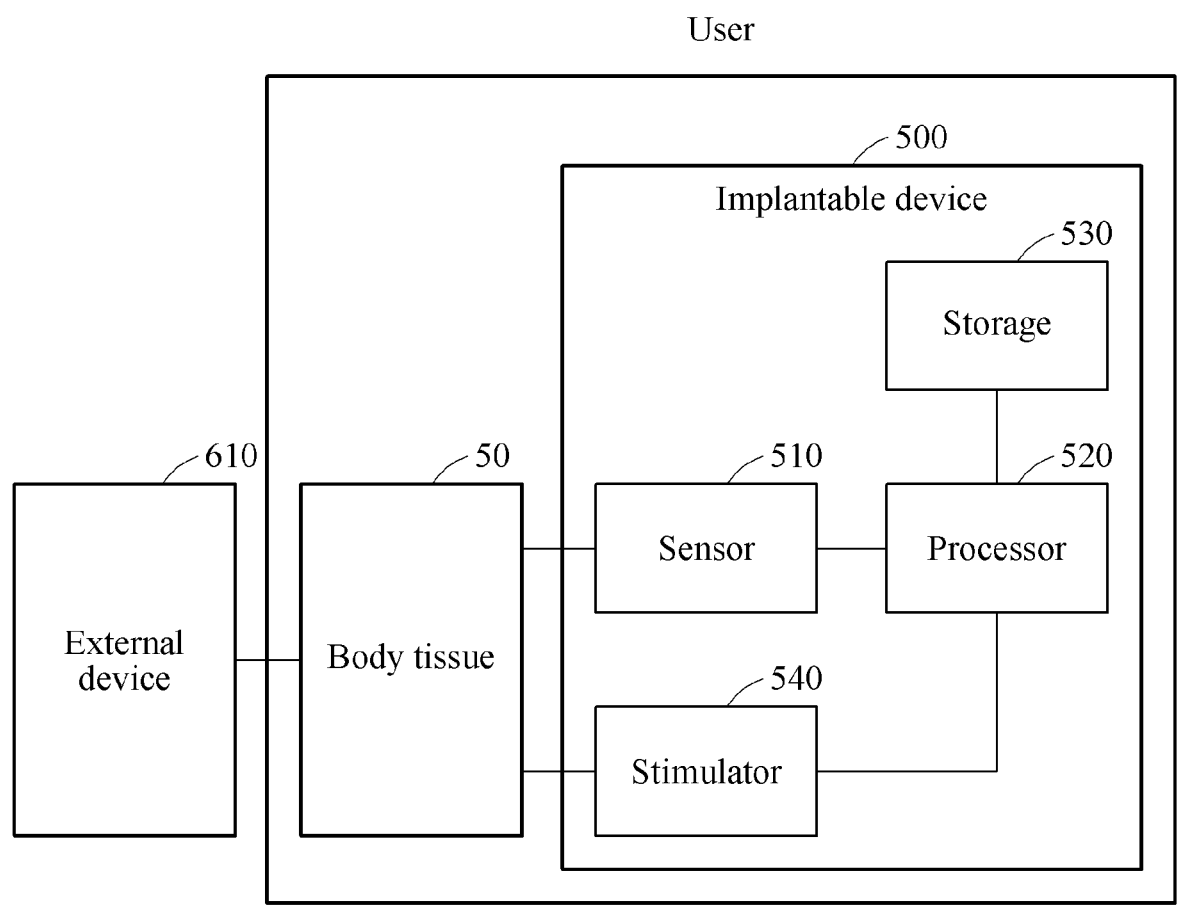
FIG. 6 is a diagram illustrating an example of an implantable device.

When the amount of the information to be transferred from the electronic wallet is great, the external device, for example, an external device 610 illustrated in FIG. 6, may closely recognize a change in the tissue of the user and receive the information, instead of the user recognizing the change in the tissue, and then transfer the received information to the user. In an example, an external camera configured to capture an image of the user may recognize a stimulus in the tissue and receive the information, instead of the user.

FIG. 5 is a diagram illustrating an example of an implantable device. Referring to FIG. 5, an implantable device 500 includes a sensor 510, a processor 520, a storage 530, and a stimulator 540. Although not illustrated, the implantable device 500 may further include a power supply (not shown).

Figure 7:
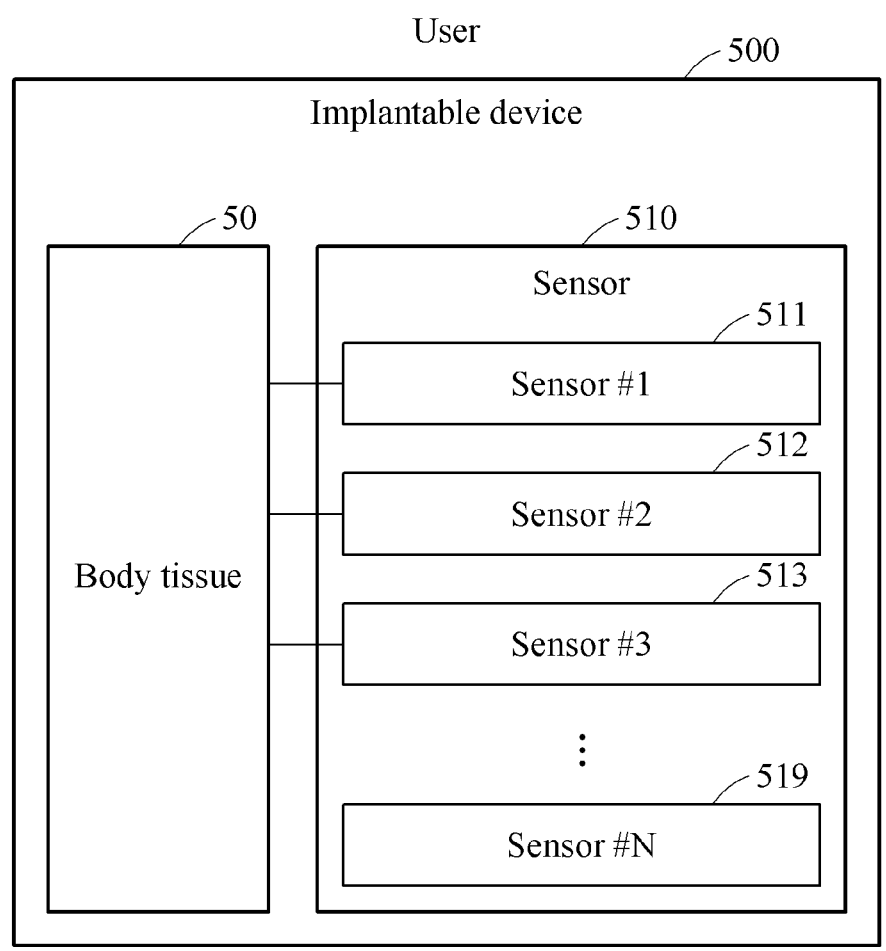
FIG. 7 is a diagram illustrating an example of a sensor of an implantable device.

The sensor 510 senses at least one neural signal generated in a tissue 50 of a body of a user. The sensor 510 may include, for example, a single sensor or a plurality of sensors, for example, sensors 511, 512, 513, . . . , and 519, as illustrated in FIG. 7. The sensors 511, 512, 513, . . . , and 519 may be distributed in regions separate from the tissue 50 by a certain distance, or densely disposed in a neighboring region within a certain distance.

The sensor 510 includes one or more sensors including, for example, an implantable sensor and a patch-type contact sensor. The sensors may include, for example, a sensor including a measurement electrode configured to sense an electrical signal in the body that is generated in the tissue 50, and/or a biosensor configured to sense enzyme, antigen, antibody, and other chemical substances such as a hormone and a neurotransmitter that are present in the tissue 50 or to sense a chemical signal. The sensors may be positioned in a body tissue of the user that may be readily controllable by an intention of the user.

The processor 520 analyzes the neural signal sensed through the sensor 510, and recognizes input information to process a cryptocurrency-based financial transaction and processes the cryptocurrency-based financial transaction based on the recognized input information. The processor 520 may process an instruction input from the user, generate an invoice to transfer a cryptocurrency using cryptocurrency-related information input from the user, or generate electronic signature information.

The storage 530 stores the cryptocurrency-related information including, for example, a private key of the user and a cryptocurrency address of the user.

Figure 8:
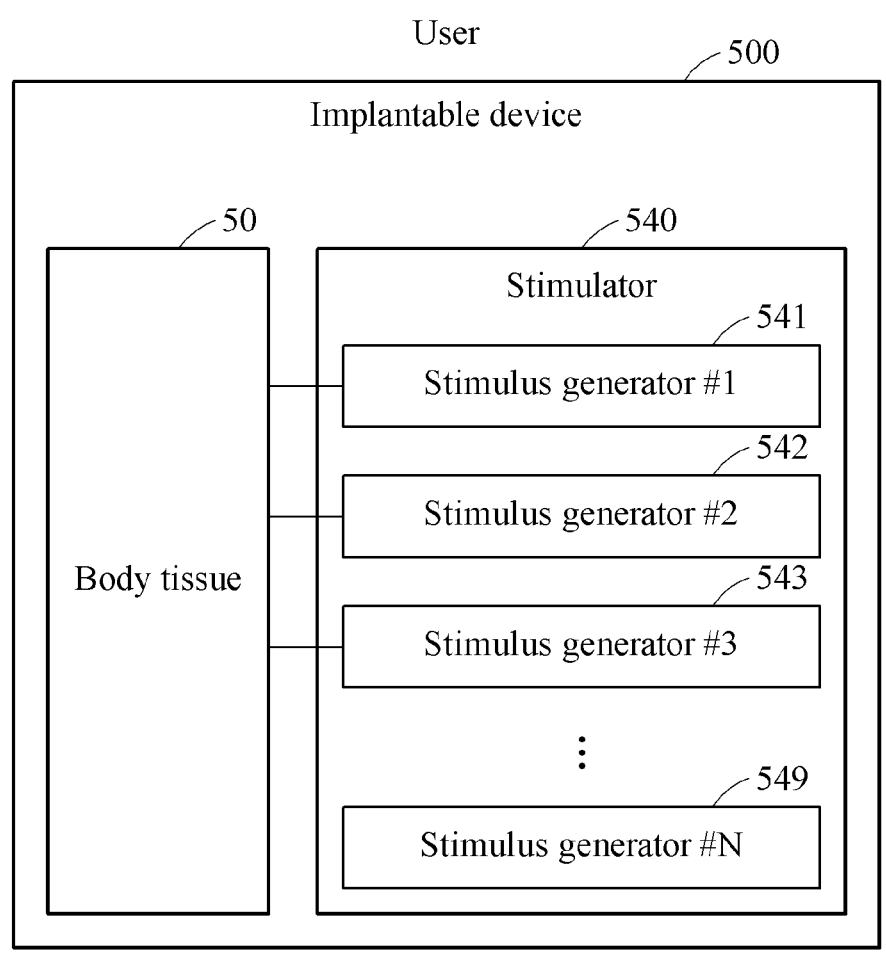
FIG. 8 is a diagram illustrating an example of a stimulator of an implantable device.

The stimulator 540 generates a stimulus signal, which is an output signal to be transferred to the user. The output signal may be a biosignal that is not controllable by the intention of the user. The stimulator 540 may include a single stimulus generator, or a plurality of stimulus generators, for example, stimulus generators 541, 542, 543, . . . , and 549 as illustrated in FIG. 8. The stimulus generators 541, 542, 543, . . . , and 549 may be distributed in regions separate from the tissue 50 by a certain distance, or densely disposed in a neighboring region within a certain distance.

The stimulus generators of the stimulator 540 may include, for example, a stimulus electrode. The stimulator 540 may be positioned at a body tissue that may be readily recognized by the user or readily measured by an external device.

The power supply may include an implantable battery and a battery charger. The battery charger may generate power to be used to charge the implantable battery, and generate power by receiving wireless power from the external device. In another example, the battery charger may generate power based on, for example, a body temperature, a body movement, and a chemical substance in the body.

The power supplied through the power supply may be used to supply power to operate the sensor 510, the processor 520, and the stimulator 540.

FIG. 6 is a diagram illustrating another example of an implantable device. Referring to FIG. 6, an implantable device 500 may operate in connection with an external device 610. The implantable device 500 may be the same as the one illustrated in FIG. 5, and thus only operations of the implantable device 500 that are performed differently from those of the one illustrated in FIG. 5 by being connected to the external device 610 will be described hereinafter. In addition to the description of FIG. 6 below, the descriptions of FIG. 5 is also applicable to FIG. 6 and are incorporated herein by reference. Thus, the above description may not be repeated here.

The external device 610 includes a power supply, a processor, and a communication interface. The external device 610 may support a function of transmitting and receiving a greater quantity of data through the communication interface. In addition, the external device 610 may support a function of processing a greater quantity of data. The external device 610 may be a user device such as, for example, a smartphone or a wearable device. For example, in a case in which the implantable device 500 does not include a separate power supply, the implantable device 500 may receive power through wireless communication with the external device 610.

The external device 610 may include a function of recognizing a change in biosignal of the user and/or a function of generating a stimulus signal for the user. For example, when an amount of sensed neural signal(s) in a tissue of a body of the user is determined to exceed a processing capacity of the implantable device 500, the implantable device 500 may sense the neural signal through the function of the external device 610 that recognizes a change in biosignal. In another example, when an amount of information of a result of performing a cryptocurrency-based financial transaction is determined to exceed a processing capacity of the implantable device 500, the implantable device 500 may allow the user to recognize the result of performing the cryptocurrency-based financial transaction through the external device 610.

FIG. 7 is a diagram illustrating an example of a sensor of an implantable device. Referring to FIG. 7, a sensor 510 includes a plurality of sensors 511, 512, 513, . . . , and 519.

An implantable device may combine results indicating changes in a tissue of a body of a user, for example, neural signals, that are measured by the sensors 511, 512, 513, . . . , and 519 of the sensor 510. The implantable device may recognize and/or receive input information transmitted from the user based on a result of combining the neural signals that are measured by the sensors. The input information may be, for example, an instruction signal that triggers certain function to process a cryptocurrency-based financial transaction, or information to process the cryptocurrency-based financial transaction.

FIG. 8 is a diagram illustrating an example of a stimulator of an implantable device. Referring to FIG. 8, a stimulator 540 includes a plurality of stimulus generators 541, 542, 543, . . . , and 549.

An implantable device may combine a plurality of stimulus signals generated through the stimulus generators 541, 542, 543, . . . , and 549, and transfer information to a user based on a result of combining the stimulus signals generated through the stimulus generators.

Figure 9:
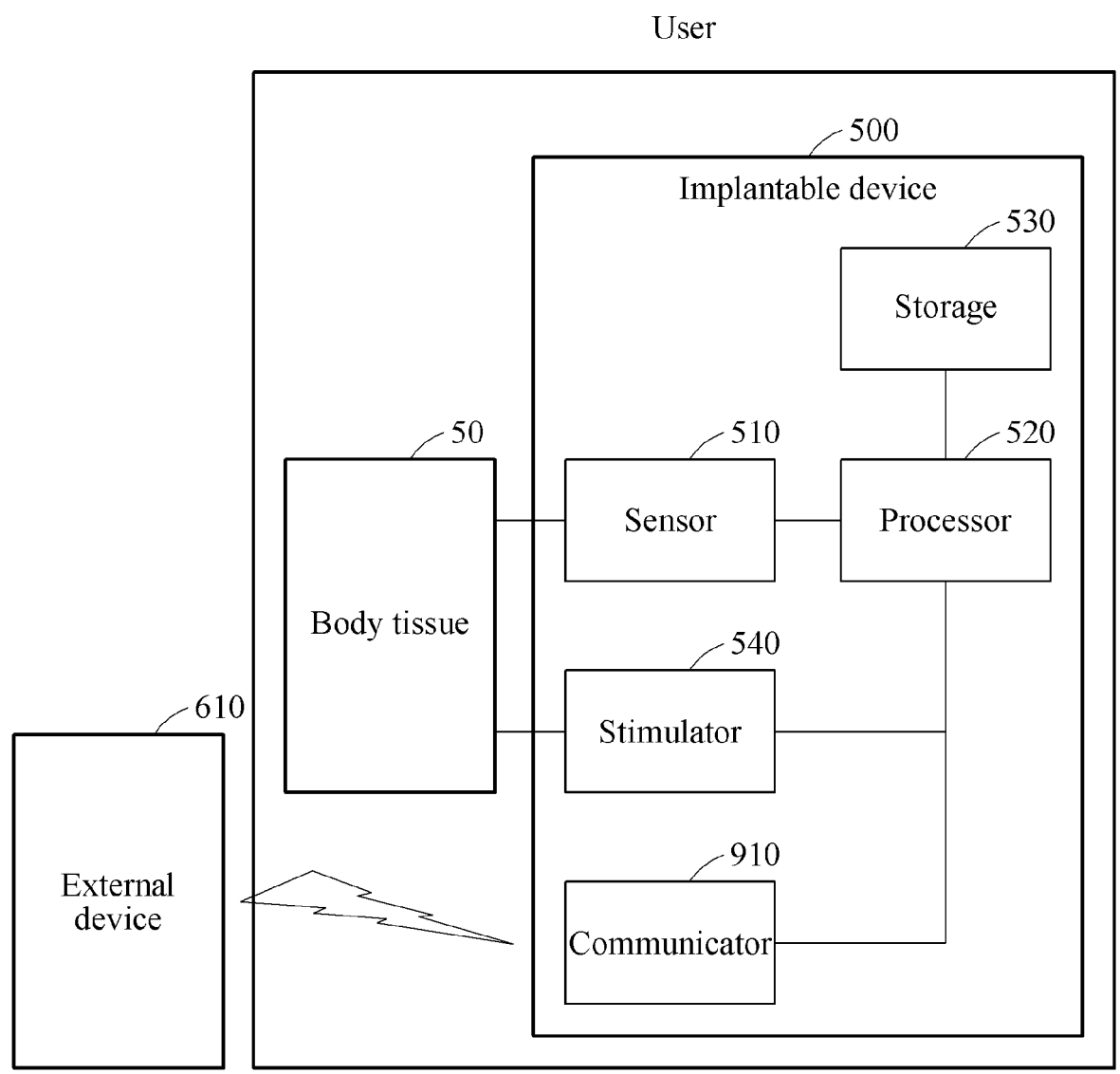
FIG. 9 is a diagram illustrating an example of an implantable device.

FIG. 9 is a diagram illustrating another example of an implantable device. An implantable device illustrated in FIG. 9 is the same as the implantable device 500 illustrated in FIGS. 5 and 6, other than a communicator 910 illustrated in FIG. 9. Thus, an operation of the communicator 910 will be described hereinafter. In addition to the description of FIG. 9 below, the descriptions of FIGS. 5-6 are also applicable to FIG. 9 and are incorporated herein by reference. Thus, the above description may not be repeated here.

The communicator 910 receives information needed to transfer a cryptocurrency from an external device 610 through wireless communication. The information needed to transfer a cryptocurrency may include, for example, information on an account to which the cryptocurrency is to be transferred and an amount of money that is to be transferred.

In an example, a final decision signal or a final decision instruction to perform a payment of a cryptocurrency may be generated based on a neural signal of a user. A result of performing the payment of the cryptocurrency may be transferred to the user based on a neural signal stimulus. In an example, detailed information related to the payment of the cryptocurrency, for example, generated invoice data, may be transferred to the external device 610 through the communicator 910.

Figure 10:
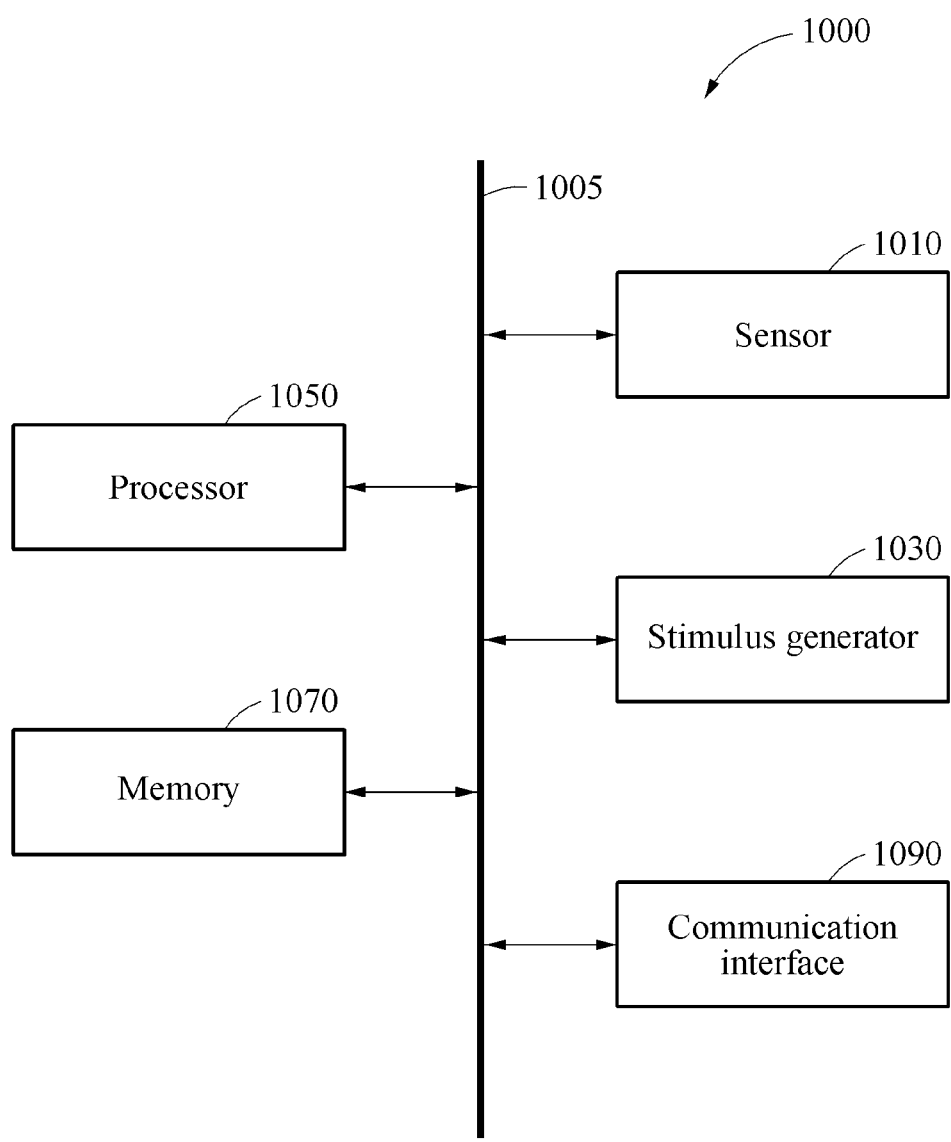
FIG. 10 is a diagram illustrating an example of an implantable device.

FIG. 10 is a diagram illustrating an example of an implantable device. Referring to FIG. 10, an implantable device 1000 includes at least one sensor 1010, and a processor 1050. The implantable device 1000 further includes at least one stimulus generator 1030, a memory 1070, and a communication interface 1090. The sensor 1010, the stimulus generator 1030, the processor 1050, the memory 1070, and the communication interface 1090 may communicate with one another through a communication bus 1005.

The sensor 1010 senses at least one neural signal generated in a tissue of a body of a user. The sensor 1010 may sense a neural signal generated to induce a movement of the tissue based on an intention of the user, or sense a neural signal generated in at least a portion of the body of the user based on at least one of the intention of the user or a muscular movement based on the intention of the user. In another example, the sensor 1010 may sense a neural signal generated in a certain pattern based on at least one of the intention of the user or the muscular movement based on the intention of the user. The sensor 1010 may sense a neural signal generated in a certain pattern in at least a portion of the body of the user based on at least one of the intention of the user or the muscular movement based on the intention of the user.

The stimulus generator 1030 generates a stimulus signal to transfer, to the user, a result of processing or performing a cryptocurrency-based financial transaction.

The processor 1050 allows the user to recognize the reception of the result of performing the cryptocurrency-based financial transaction through the stimulus signal. The stimulus signal may include, for example, a neural stimulus signal associated with an involuntary muscle of the user, a neural stimulus signal connected to a portion of the body of the user, a neural stimulus signal to induce a movement of a muscle not intended by the user, a stimulus signal to induce a movement in a certain pattern for a muscle not intended by the user, and a neural stimulus signal to induce a tactile stimulus not experienced by the user.

The processor 1050 recognizes input information to process the cryptocurrency-based financial transaction by analyzing the neural signal. The processor 1050 processes the cryptocurrency-based financial transaction based on the input information.

The processor 1050 analyzes whether the neural signal is a first neural signal corresponding to a function of making a payment with a cryptocurrency, a second neural signal corresponding to a function of transferring a cryptocurrency, or a third neural signal corresponding to a function of processing another financial transaction that does not involve a cryptocurrency. When the neural signal is the first neural signal, the processor 1050 may recognize the neural signal as input information to control the implantable device 1000 corresponding to an electronic wallet to make a payment with a cryptocurrency. When the neural signal is the second neural signal, the processor 1050 may recognize the neural signal as input information to draft an invoice corresponding to a first account address to which a cryptocurrency is to be transferred. When the neural signal is the third neural signal, the processor 1050 may recognize the neural signal as input information to process another financial transaction not involving a cryptocurrency.

The memory 1070 stores cryptocurrency-related information including at least one of a private key of the user or an account address of a cryptocurrency of the user.

Although not illustrated, the implantable device 1000 may further include an external device (not shown) configured to sense a neural signal. When the implantable device 1000 further includes the external device, the implantable device 1000 may receive information from the external device through the communication interface 1090, or transmit information through the external device.

For example, the processor 1050 may determine whether an amount of sensed neural signal(s) exceeds a processing capacity of the implantable device 1000. In this example, when the amount of sensed neural signal(s) exceeds the processing capacity of the implantable device 1000, the implantable device 1000 may sense a neural signal by further using the external device.

In addition, the processor 1050 may perform at least one or all of the operations described above with reference to FIGS. 1A through 9, or an algorithm corresponding to the at least one or all of the operations. The processor 1050 may be a data processing device that is embodied by hardware having a circuit of a physical structure to perform desired operations. The desired operations may include, for example, a code or instructions included in a program. The data processing device embodied by hardware may include, for example, a microprocessor, a central processing unit (CPU), a processor core, a multi-core processor, a multiprocessor, an application-specific integrated circuit (ASIC), a field programmable gate array (FPGA), and the like. Further details of the processor 1050 is provided below.

The processor 1050 may execute a program, and control the implantable device 1000. A code of the program executed by the processor 1050 may be stored in the memory 1070.

The memory 1070 may store various sets of information generated in a processing operation of the processor 1050. In addition, the memory 1070 may store various sets of data and programs. The memory 1070 may include a volatile memory or a nonvolatile memory. The memory 1070 may have a massive storage medium such as a hard disk to store various sets of data.

The implantable device, and other apparatuses, units, modules, devices, and other components described herein with respect to FIGS. 5-10 are implemented by hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1A and 1B, and 2-4 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In an example, the instructions or software includes at least one of an applet, a dynamic link library (DLL), middleware, firmware, a device driver, an application program storing the method of operating an implantable device. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions used herein, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, card type memory such as multimedia card, secure digital (SD) card, or extreme digital (XD) card, magnetic tapes, floppy disks, magneto-optical data storage devices, optical data storage devices, hard disks, solid-state disks, and any other device that is configured to store the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of operating an implantable device, comprising:
   sensing, by the implantable device, a first neural signal generated in a tissue of a body;
   recognizing, by the implantable device, first input information by analyzing the first neural signal;
   determining, by the implantable device, whether the first neural signal corresponds to making a payment with a cryptocurrency;
   in response to the determining of the first neural signal corresponding to the making of the payment with the cryptocurrency, processing, by the implantable device, a cryptocurrency based financial transaction based on the first input information by making the payment with the cryptocurrency
   sensing, by the implantable device, a second neural signal generated in the tissue of the body;
   recognizing, by the implantable device, second input information by analyzing the second neural signal;
   determining, by the implantable device, whether the second neural signal corresponds to transferring the cryptocurrency; and
   in response to the determining of the second neural signal corresponding to the transferring of the cryptocurrency, processing, by the implantable device, the cryptocurrency-based financial transaction based on the second input information by drafting an invoice for a first account address to which the cryptocurrency is to be transferred.

2. The method of claim 1, wherein any one or any combination of the first neural signal and the second neural signal is generated based on at least one of an intention of a user or a muscular movement based on the intention of the user.

3. The method of claim 1, wherein any one or any combination of the first neural signal and the second neural signal comprises at least one of:
   an electrical signal in the body including an electroencephalogram (EEG) signal and an electromyogram (EMG) signal; or
   a chemical signal in the body including a hormone and a neurotransmitter.

4. The method of claim 1, wherein the sensing of any one or any combination of the first neural signal and the second neural signal comprises:
   sensing any one or any combination of the first neural signal and the second neural signal or a change in any one or any combination of the first neural signal and the second neural signal using a sensor of the implantable device implanted in the tissue of the body.

5. The method of claim 1, wherein the sensing of any one or any combination of the first neural signal and the second neural signal comprises at least one of:
   sensing a neural signal generated to induce a movement of the tissue based on an intention of a user;
   sensing a neural signal generated in a portion of the body of the user based on any one or any combination of the intention of the user or a muscular movement based on the intention of the user;
   sensing a neural signal generated in a pattern based on any one or any combination of the intention of the user or the muscular movement based on the intention of the user; or
   sensing a neural signal generated in a pattern in at least one portion of the body of the user based on at least one of the intention of the user or the muscular movement based on the intention of the user.

6. The method of claim 1, wherein the sensing of any one or any combination of the first neural signal and the second neural signal comprises:
   sensing neural signals through channels in the tissue of the body of the user.

7. The method of claim 1, further comprising:
   sensing, by the implantable device, a third neural signal generated in a tissue of a body;
   analyzing whether the third neural signal corresponds to a financial transaction not involving the cryptocurrency.

8. The method of claim 1, wherein the processing of the cryptocurrency-based financial transaction comprises:
   receiving the first account address to which the cryptocurrency is to be transferred;
   generating the invoice corresponding to the first account address based on cryptocurrency-related information comprising a second account address of the cryptocurrency of the user and a private key of the user; and
   performing an electronic signature on the invoice by generating electronic signature information.

9. The method of claim 7, further comprising:
   processing, by the implantable device, the financial transaction not involving the cryptocurrency, in response to the third neural signal corresponding to the financial transaction not involving the cryptocurrency.

10. The method of claim 9, wherein the processing of the financial transaction not involving cryptocurrency comprises:
    inputting a password to process the financial transaction; and performing an electronic signature to process the financial transaction by generating electronic signature information.

11. The method of claim 1, further comprising:
generating a stimulus signal to transfer a result of processing the cryptocurrency-based financial transaction to the body of a user; and
recognizing the result of processing the cryptocurrency-based financial transaction, in response to the generated stimulus signal.

12. The method of claim 11, wherein the generating of the stimulus signal comprises at least one of:
generating a neural stimulus signal associated with an involuntary muscle of the user;
generating a neural stimulus signal connected to a portion of the body of the user;
generating a neural stimulus signal to induce a movement of a muscle not intended by the user;
generating a stimulus signal to induce a movement in a pattern for a muscle not intended by the user; or
generating a neural stimulus signal to induce a tactile stimulus not experienced by the user.

13. The method of claim 11, wherein the recognizing of the result of the processing of the cryptocurrency-based financial transaction further comprises:
determining whether an amount of information of the result of processing the cryptocurrency-based financial transaction exceeds a processing capacity of the implantable device; and
recognizing the result of processing the cryptocurrency-based financial transaction using an external device, in response to the determining that the amount of the information exceeds the processing capacity of the implantable device.

14. A non-transitory computer-readable storage medium storing instructions that, when executed by one or more processors, cause the one or more processors to perform the operating method of claim 1.

15. An implantable device comprising:
at least one sensor configured to sense a first neural signal and a second neural signal generated in a tissue of a body; and
a processor configured to
recognize first input information by analyzing the first neural signal,
determine whether the first neural signal corresponds to making a payment with a cryptocurrency,
in response to the determining of the first neural signal corresponding to making the payment with the cryptocurrency, process a cryptocurrency-based financial transaction based on the first input information by making the payment with the cryptocurrency,
recognize second input information by analyzing the second neural signal,
determine whether the second neural signal corresponds to transferring the cryptocurrency; and
in response to the determining of the second neural signal corresponding to the transferring of the cryptocurrency, process the cryptocurrency-based financial transaction based on the second input information by drafting an invoice for a first account address to which the cryptocurrency is to be transferred.

16. The implantable device of claim 15, wherein the at least one sensor is further configured to sense any one or any combination of the first neural signal and the second neural signal based on any one or any combination of:
a neural signal generated to induce a movement of the tissue based on an intention of a user;
a neural signal generated in a portion of the body of the user based on any one or any combination of the intention of the user or a muscular movement based on the intention of the user;
a neural signal generated in a pattern based on any one or any combination of the intention of the user or the muscular movement based on the intention of the user; or
a neural signal generated in a pattern in at least one portion of the body of the user based on at least one of the intention of the user or the muscular movement based on the intention of the user.

17. The implantable device of claim 15, wherein:
the at least one sensor is further configured to sense a third neural signal generated in the tissue of the body; and
the processor is further configured to analyze whether the third neural signal corresponds to a financial transaction not involving the cryptocurrency.

18. The implantable device of claim 15, wherein the processor is further configured to:
recognize the input information as being for processing the financial transaction not involving the cryptocurrency, in response to the third neural signal corresponding to the financial transaction not involving the cryptocurrency.

19. The implantable device of claim 15, further comprising:
a stimulus generator configured to generate a stimulus signal to transfer a result of processing the cryptocurrency-based financial transaction to the body of a user, and
the processor is further configured to recognize the result of processing the cryptocurrency-based financial transaction, in response to the generated stimulus signal.

20. The implantable device of claim 19, wherein the stimulus signal comprises at least one of:
a neural stimulus signal associated with an involuntary muscle of the user;
a neural stimulus signal connected to a portion of the body of the user;
a neural stimulus signal to induce a movement of a muscle not intended by the user;
a stimulus signal to induce a movement in a pattern for a muscle not intended by the user; or
a neural stimulus signal to induce a tactile stimulus not experienced by the user.

21. The implantable device of claim 19, wherein the processor is further configured to:
determine whether an amount of information of the result of processing the cryptocurrency-based financial transaction exceeds a processing capacity of the implantable device; and
recognize the result of processing the cryptocurrency-based financial transaction by further using an external device, in response to the determination that the amount of the information exceeds the processing capacity of the implantable device.

22. The implantable device of claim 15, further comprising:
a memory configured to store cryptocurrency-related information comprising at least one of a private key of the user or an account address of a cryptocurrency of the user.

* * * * *